(12) United States Patent
Arai

(10) Patent No.: US 10,502,709 B2
(45) Date of Patent: Dec. 10, 2019

(54) ELECTROPHORESIS DEVICE

(71) Applicant: SHIMADZU CORPORATION, Kyoto-shi (JP)

(72) Inventor: Akihiro Arai, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 239 days.

(21) Appl. No.: 15/418,195

(22) Filed: Jan. 27, 2017

(65) Prior Publication Data
US 2018/0217093 A1 Aug. 2, 2018

(51) Int. Cl.
*G01N 27/447* (2006.01)

(52) U.S. Cl.
CPC . *G01N 27/44717* (2013.01); *G01N 27/44743* (2013.01)

(58) Field of Classification Search
None
See application file for complete search history.

(56) References Cited

U.S. PATENT DOCUMENTS

2011/0117127 A1* 5/2011 Kost ............... G01N 27/44743
424/209.1

FOREIGN PATENT DOCUMENTS

JP 2008-89440 A 4/2008

OTHER PUBLICATIONS

Dose et al. (Anal. Chem., 63, 1154-1158) (Year: 1991).*
Lee et al. (Anal. Chem., 64, 1226-1231) (Year: 1992).*

* cited by examiner

*Primary Examiner* — Luan V Van
*Assistant Examiner* — Steven E Rosenwald
(74) *Attorney, Agent, or Firm* — Sughrue Mion, PLLC

(57) ABSTRACT

The electrophoresis method includes the following steps: electrically injecting a sample into an electrophoresis flow path through one end thereof; subjecting the injected sample to electrophoresis to be separated by applying a voltage to both ends of the electrophoresis flow path; detecting the separated sample component at a detection position of the electrophoresis flow path; obtaining a peak area of the detected sample component; and correcting the obtained peak area on the basis of an injection rate of each sample component. Correction based on the injection rate includes, a correction based on a relative mobility of the sample component and at least one of: a correction based on the linear velocity at the time of sample injection for each sample component and a correction based on the current integral value at the time of sample injection.

8 Claims, 11 Drawing Sheets

ELECTROPHORESIS DEVICE

TECHNICAL FIELD

The present invention relates to an electrophoresis device that performs an electrophoresis on a plate (chip) in which a capillary electrophoresis device or a flow path is subjected to micro processing.

BACKGROUND ART

In a capillary electrophoresis device in general, a fused silica capillary having 100 μm or less in inner diameter is filled up with a separation medium (an electrophoresis buffer solution or an electrophoresis buffer solution containing a sieving polymer solution), and a sample is introduced into one end of the capillary, after which a voltage is applied to both ends of the capillary to perform an electrophoresis of the sample within the capillary so as to separate [the sample]. The temperature in the periphery of the capillary is kept constant for the stabilization of the separation performance in the capillary. The analyte component separated in the capillary is detected on the other end side of the capillary by other optical or electrochemical fluorescence technique. The capillary electrophoresis device may have one capillary or a plurality of capillaries mounted.

The plate used for an electrophoresis is equipped with, for example, a substrate provided with an electrophoresis flow path in the inside; and a pair of reservoirs that are arranged at both ends of the electrophoresis flow path, used for storing an electrophoresis buffer solution, and electrically conducted to the end part of the electrophoresis flow path via the electrophoresis buffer solution (see Patent Literature 1). One or a plurality of electrophoresis flow paths may be provided to one substrate.

There is an electric injection method (an electrokinetic injection method: EKI method) as one of the methods of introducing a sample to a flow path formed in a capillary or a plate (for example, see Non-Patent Literature 1). In the electric injection method, a voltage for a certain period of time is applied to two electrodes, in a state where one end (injection end) of the electrophoresis flow path filled up with a separation medium is brought in contact with a sample, while the other end of the electrophoresis flow path is brought in contact with a buffer solution, and the electrodes are brought in contact with each of the sample and the buffer solution, thereby introducing the sample of a specified quantity into the flow path.

After the sample is introduced into the electrophoresis flow path, the electrophoresis of the sample is performed by bringing the sample injection end in contact with the buffer solution, immersing the electrodes in the buffer solution in each reservoir provided at both ends of the electrophoresis flow path, and applying a voltage to the two electrodes.

PRIOR ART LITERATURE

Patent Literature

[Patent Literature 1] Japanese Unexamined Patent Application Publication 2008-89440

Non-Patent Literatures

[Non-Patent Literature 1] Protein nucleic acid enzyme, 38 (3), 2243 (1993)

[Non-Patent Literature 2] Anal. Chem., 1998, 70, 2248-2253

SUMMARY OF INVENTION

Problem to be Solved by the Invention

Since in the electric injection method, the quantitative relation of the sample component introduced differs from the original composition of the sample according to the difference of the mobility of the sample component, quantification is theoretically difficult.

If the relative mobility of any component with respect to an internal standard substance is known, it is also possible to correct the effective injection volume to a certain degree; however, since it is limited to when the injection rate and the temperature at the time of injection are constant, a restrictive correction becomes inevitable. Moreover, the correction becomes still more difficult in cases when the ionic strength of a sample differs from that of a separation buffer solution, when a sample is injected into a separation medium containing an intercalator pigment, or when the mobility at the time of injection changes.

By dividing a portion of a capillary and using an electroosmotic flow like a simulated pump, attempts to reduce the difference of the mobility of a sample component are reported at various research levels (for example, see Non-Patent Literature 12); however, there is no example that can be put into practical use since the convenience of a capillary is impaired, and [the device] is also costly.

On the plate for a certain type of electrophoresis, a crossing flow path is arranged on a separation flow path, and after a sample introduction process is continued until the sample composition of the crossing part becomes in a steady state, the whole quantity of the sample components of the crossing part is injected. In that case, it is possible to avoid the difference in the injection volume according to the difference in mobility intrinsic to the sample component. However, it is difficult to form a crossing flow path in the case of a capillary electrophoresis device since there is also a plate for electrophoresis without having such a crossing part.

The objective of the present invention is to provide an electrophoresis method and device for injecting a sample by means of an electric injection method, subjecting a capillary electrophoresis device or a device equipped with a plate for electrophoresis without a crossing part, with which a quantitative analysis is possible.

Means for Solving the Problems

Since there are differences in the injection volume for every sample component in the samples injected by the electric injection method, in the present invention, the detected peak area is corrected based on the injection rate for every sample component. Since the peak area that has been subjected to a rate correction expresses the injection volume for every sample component, a quantitative analysis becomes possible as long as the peak area is corrected.

That is, the electrophoresis method of the present invention is a method of carrying out a quantitative analysis of sample components in which an electrophoretic separation is carried out, the method of which consists of the following steps: (A) a step of electrically injecting a sample into an electrophoresis flow path from one end thereof, (B) a step of subjecting the injected sample to electrophoresis and separation by applying a voltage to both ends of the electrophoresis flow path, (C) a step of detecting the separated sample component at a detection position of the electrophoresis flow path, (D) a step of obtaining a peak area of the detected sample component, and (E) a step of correcting the obtained peak area based on the injection rate for every sample component.

Furthermore, the correction based on the injection rate in the step (E) includes, in addition to (E1) a correction based on the relative mobility of a sample component, at least one of (E2) a correction based on the linear velocity at the time of the sample injection for every sample component and (E3) a correction based on a current integral value at the time of sample injection.

The electrophoresis device of the present invention that realizes the electrophoresis method of the present invention is equipped with an electrophoresis section provided with an electrophoresis flow path, an electric power unit for applying a voltage to both ends of the electrophoresis flow path to carry out a sample injection into one end of the electrophoresis flow path and the electrophoresis in the electrophoresis flow path, and a detector for detecting the sample component separated by the electrophoresis flow path; and the device also has a control unit that incorporates an electrophoretic signal from the detector and carries out a quantitative analysis for every sample component.

And the aforementioned control unit is provided with a peak area calculation unit for obtaining a peak area from the electrophoretic signal and a correction unit for correcting the determined peak area based on the injection rate for every sample component. The correction unit is provided with a peak area correction unit according to relative mobility for performing an injection rate-based correction based on the relative mobility of a sample component, and the correction unit is further provided with at least one of the peak area correction unit according to the linear velocity at the time of injection for performing an injection rate-based correction based on the linear velocity at the time of the sample injection for every sample component and the peak area correction unit according to a current integral value for performing an injection rate-based correction based on a current integral value.

Effect of the Invention

According to the present invention, in the electrophoresis method and device for electrically injecting a sample, the determined peak area is corrected based on the injection rate for every sample component, so quantification theoretically deemed to be difficult in the past becomes possible. And a peak area can be corrected without the need to devise a capillary or adding a crossing flow path; therefore, quantification can be carried out inexpensively without impairing convenience.

DESCRIPTION OF EMBODIMENTS

Figure 1:
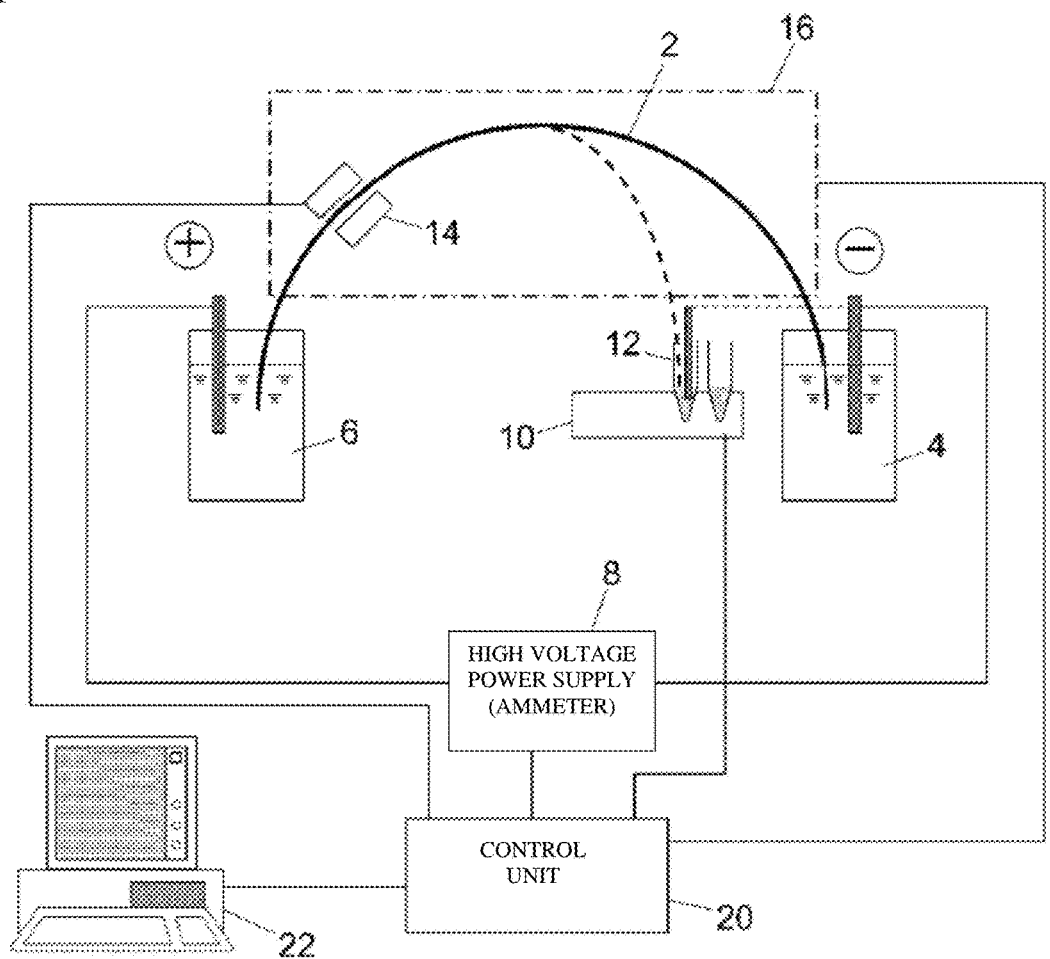
FIG. 1 is a configuration diagram schematically illustrating a capillary electrophoresis device of a first example of embodiment.

According to one embodiment, the difference in the injection volume of the sample component in an electric injection method is corrected according to the difference of the relative mobility of each ion component, and based on this correction, the determined peak area is corrected. The difference of relative mobility occurs, for example, according to the DNA strand length. If the DNA strand length differs even when the charge amount is constant, a difference in relative mobility occurs according to the difference in molecular weight.

With regard to the difference of the relative mobility of each ion component, for example, two kinds of internal standard substances at known concentrations consisting of a component with larger mobility than that of any sample component (the shortest chain length in the case of DNA) and a component with smaller mobility than that of any sample component (the longest chain length in the case of DNA) are used to calculate the relative mobility to any component. In the aforementioned step (A), namely, two kinds of internal standard substances, which are internal standard substance A with smaller mobility than that of any sample component and internal standard substances B with larger mobility than that of any sample component, are injected into the capillary along with a sample, and interpolation coefficient Fi for every sample component is used as the relative mobility in step (E). The interpolation coefficient F is a standardized coefficient in which mobility $μ_A$ of the internal standard substance A is 0 and mobility $μ_B$ of the internal standard substance B is 1. Thus, if the relative mobility correction according to two kinds of internal standards is performed, the peak area determined can also be corrected when the ionic strength of the sample is different from that of the separation buffer solution serving as a separation medium.

As another embodiment, the mobility change at the time of sample injection is corrected. For example, when a capillary is filled up with a separation medium containing an intercalator pigment, the mobility changes with the change in the charge amount according to a complex formation of a sample component and an intercalator pigment. Then, this embodiment includes the correction based on the linear velocity at the time of the sample injection for every sample component as the correction based on the injection rate. As the correction based on the linear velocity at the time of sample injection, the linear velocity conversion table obtained in advance under specific conditions can be used. The specific conditions include the type of the intercalator pigment, concentration, sample injection voltage and time, and other parameters. Thus, quantification accuracy further improves by also correcting a system containing an intercalator pigment.

In yet another embodiment, the sample injection volume is corrected according to the electric current change in a sample injection process. The current change in a sample injection process occurs according to the change in temperature and other factors. Then, this embodiment further includes a step of calculating a current integral value at the time of sample injection and includes a correction based on the current integral value calculated as the correction based on the injection rate. The linear velocity at the time of injection changes linearly with respect to the change in the electric current value in a sample injection process (where the coefficient determined by the zeta potential of a capillary/sample, pH, dielectric constant, ionic strength, viscosity, and DNA strand length is set to be constant).

The basic principle in one embodiment is to correct the injection volume for every sample component based on the relative mobility of the sample component when performing a correction based on the injection rate for every sample component to the peak area of each component obtained at the end of analysis. The injection volume of each component is specifically obtained as a peak area. When obtaining a peak area, a correction is carried out by converting a time axis to a movement speed (=which is proportional to the mobility) in a detecting point. That is, it is integrated by the movement speed (=(the injection end–the distance between the detecting points)/(electrophoretic time)) at that time at a peak height and displayed in a unit (mV·μm). It is preferable to further include either or both of the correction according to the change in mobility at the time of sample injection and the correction of the sample injection volume according to the change in electric current in a sample injection process. The peak area of each component obtained at the end of analysis or the value (the unit is arbitrary) obtained therefrom is used to quantify preferably from the known concentration value of an internal standard substance.

Thus, quantification can be substantially improved even if it is a method of electrically injecting a sample. Preferably, it can be brought close to quantification equivalent to a microchip electrophoresis using a crossing flow path.

FIG. 1 schematically expresses the capillary electrophoresis device of a first example of embodiment. In the fused quartz capillary 2, as shown by the solid line at the time of electrophoresis, both ends of the capillary 2 are immersed in the electrophoresis buffer solutions 4 and 6, respectively, and an electrophoresis voltage is applied to the both ends of the capillary 2 via both electrophoresis buffer solutions 4 and 6 from the high voltage power supply 8. The high voltage power supply 8 is provided with an ammeter for detecting the current that flows through the capillary 2.

An automatic sampler 10 is provided in order to inject a sample into one end of the capillary 2 prior to electrophoresis. The automatic sampler 10 holds a plurality of specimen containers 12 in a sample plate and moves the specimen containers 12 stored with the samples to be analyzed to a sample injection position. At the time of sample injection, one end of the capillary 2 is immersed in the sample of the specimen container 12 as shown by the dashed line, electrodes are also immersed in the sample 12, and a voltage for a sample injection is applied to between the sample 12 and the electrophoresis buffer solution 6. In this way, the sample is injected into one end of the capillary 2.

A detector 14 is arranged in the detection position of the other end side of the capillary 2. The detector 14 is a UV detector (ultraviolet-visible absorptiometer), for example.

The capillary 2 is stored in a thermostat 16 and maintained at a constant temperature.

A control unit 20 is provided to control the operation of the automatic sampler 10, the application of the sample injection voltage by the high voltage power supply 8, and the application of the electrophoresis voltage by the high voltage power supply 8, as well as to carry out data processing by incorporating the electrophoretic signal of the detector 14 and to perform an identification and quantification of the sample component separated by electrophoresis. A dedicated computer 22 for this capillary electrophoresis device is connected to the control unit 20.

Figure 2:
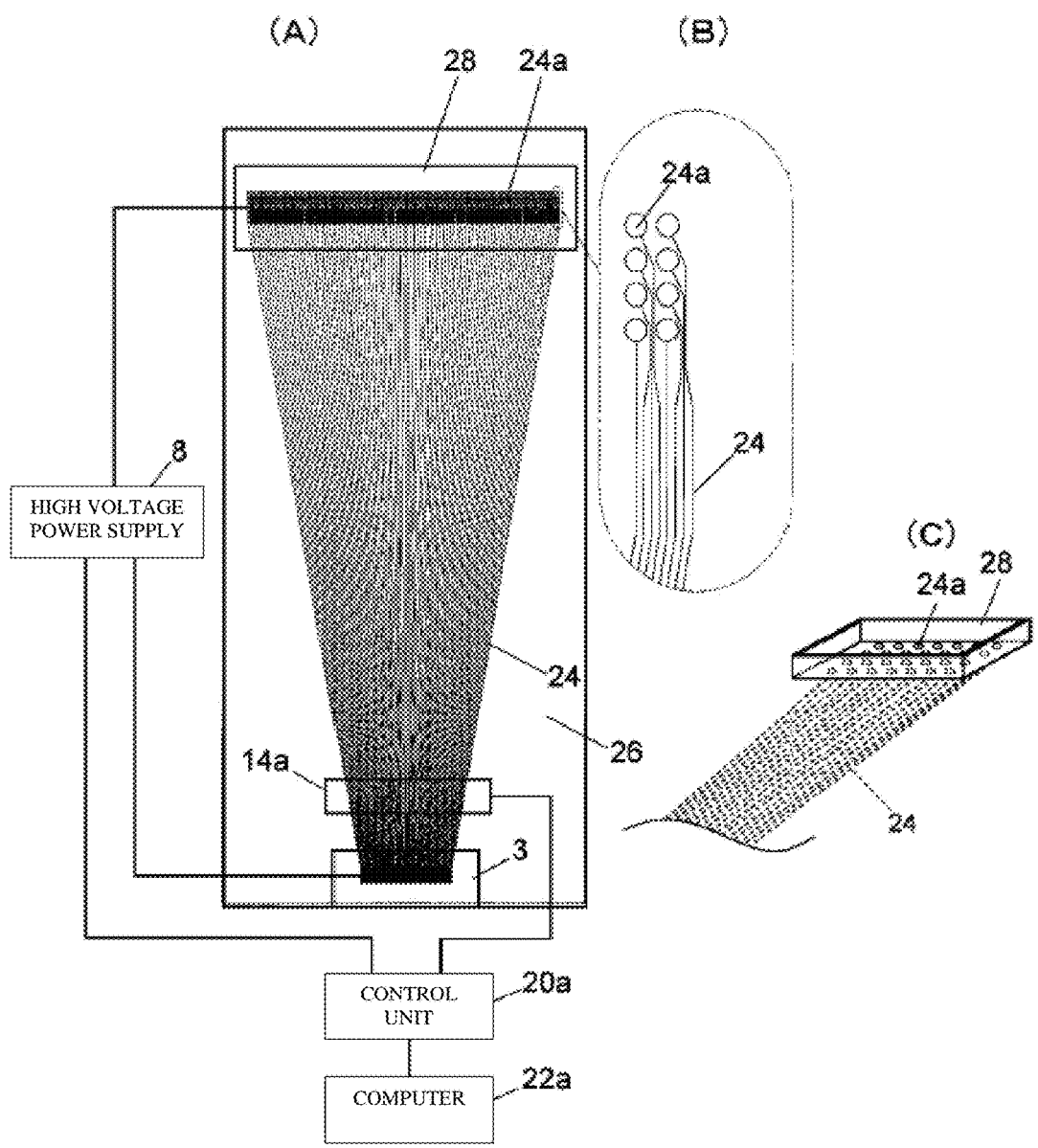
FIG. 2 includes drawings of an electrophoresis device of a second example of embodiment, (A) is a drawing in which the plate for electrophoresis is shown in a plan view and the control device is shown in a block diagram, (B) is an enlarged view of the sample injection end of the plate for electrophoresis, and (C) is an outline perspective view showing the sample injection end side.

FIG. 2 shows examples of the plate used in the electrophoresis device of a second example of embodiment at (A) and at (B). A plurality of electrophoresis flow paths 24 is arranged inside the glass substrate 26 so as not to cross one another, and on the surface of the glass substrate 26, a reservoir 28 is mounted to the end of the electrophoresis flow path 24 on the cathode side, and a reservoir 3 is mounted to the end on the anode side. A plurality of, for example, 384, electrophoresis flow paths 24 having a width of 90 μm and a depth of 40 μm are arranged so as to extend in the longitudinal direction of the glass substrate 26 and not to cross one another in a radial region spreading toward the cathode side from the anode side.

Each of the reservoirs 28 and 3 constitutes a container having an opening at the top, is used to store an electrophoresis buffer solution and configured so as to electrically conduct with the end of the electrophoresis flow path 24 via the electrophoresis buffer solution at the bottom. A plurality of, in this example, 384, openings 24a connected to the ends of the electrophoresis flow paths 24 at the bottom thereof are arranged on the reservoir 28 on the cathode side, and those openings 24a serve as a sample dispensation position. The reservoir 28 is one container surrounding an area where all the openings 24a are arranged. The reservoir 3 on the anode side is also connected to the other end of the electrophoresis flow paths 24 at the bottom thereof.

Silica glass and borosilicate glass can be used as a material of the glass substrate 26, and those made of other materials such as resin can also be used in place of the glass substrate 26. The glass substrate 26 made of a transparent material was chosen here since the components to which electrophoretic separation was carried out were detected optically; however, when a detection means other than an optical detector is used, the material of the glass substrate 26 is not limited to those being transparent.

The glass substrate 26 can be constituted by laminating two sheets of glass plates together. The electrophoresis flow path 24 can be formed on the bonding surface of one glass plate by lithography and etching (wet etching or dry etching). The opening 24a can be formed as a through hole in the position of both ends of the electrophoresis flow path 24 with another glass plate or the same glass plate by methods such as sandblasting and laser drill.

A sample is injected into the opening 24a for sample dispensation by a pipettor mechanism in order to inject the sample into one end of the electrophoresis flow path 24 prior to electrophoresis. Subsequently, the tip of each electrode is immersed in the sample currently injected in the opening 24a for sample dispensation, a predetermined voltage is applied to between the electrodes immersed in an electrophoresis buffer solution of the anode reservoir 3, and the sample is introduced into the electrophoresis flow path 24.

Next, after the sample that remains in the opening 24a for sample dispensation is removed by being sucked by the suction mechanism of an aspirator, or the like, an electrophoresis buffer solution is supplied in the cathode reservoir 3. In an electrophoretic separation, both ends of the electrophoresis flow path 24 are electrically connected to the electric power unit 8 via the electrodes inside the electrophoresis buffer solution to initiate an electrophoresis.

A detector 14a, such as a laser excitation fluorescence detector, or the like, is disposed in the detection position on the cathode reservoir 3 side of the electrophoresis flow path 24.

As in the example of embodiment shown in FIG. 1, a control unit 20a is provided to control a sample injecting operation into the opening 24a for sample dispensation, the application of the sample injection voltage by the high voltage power supply 8, and the application of the electrophoresis voltage by the high voltage power supply 8, as well as to carry out data processing by incorporating the electrophoretic signal of the detector 14a and to perform an identification and quantification of the sample component separated by the electrophoresis. A dedicated computer 22a for this electrophoresis plate electrophoresis device is connected to the control unit 20a.

Since the control units 20 and 20a and the computers 22 and 22a perform the same function during data processing for correction in one embodiment, they will be described below in a collective manner.

Figure 3:
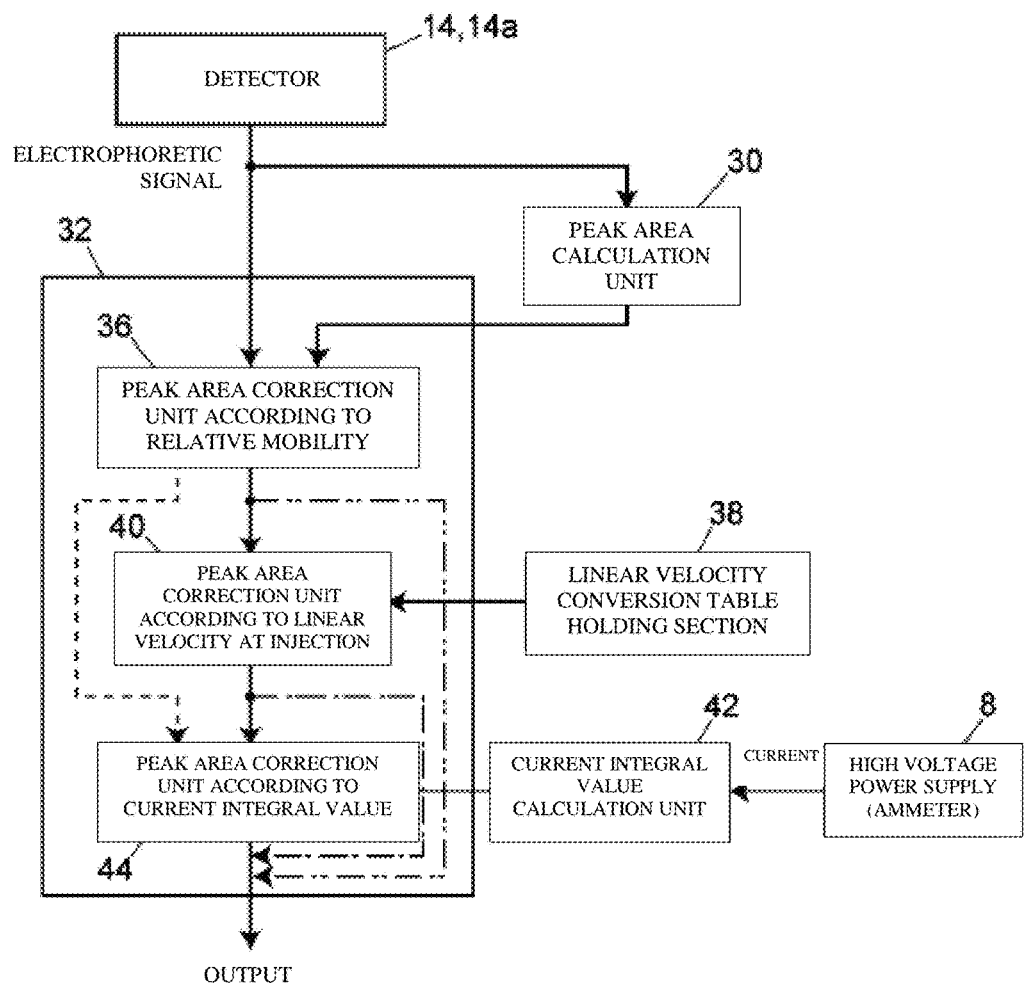
FIG. 3 is a block diagram showing the control unit in a first example of embodiment and second example of embodiment together with a detector and a high voltage power supply.

The control units 20 and 20a are provided with a peak area calculation unit 30 and a correction unit 32 as shown in FIG. 3. The peak area calculation unit 30 is constituted so that the peak area is obtained from the electrophoretic signal detected by the detectors 14 and 14a. The peak area corresponds to the injection volume of the sample component. The correction unit 32 is configured so that the peak area calculated by the peak area calculation unit 30 is corrected based on the injection rate for every sample component.

The correction unit 32 is provided with a peak area correction unit 36 according to relative mobility, and the peak area correction unit 36 according to relative mobility corrects the peak area of each sample component calculated by the peak area calculation unit 30 based on the relative mobility of each sample component.

As is also applicable to those in which the electrophoresis flow paths 2 and 24 are filled up with a separation medium containing an intercalator pigment, the correction unit 32 is preferably provided with a peak area correction unit 40 according to the linear velocity at the time of injection. The peak area correction unit 40 according to the linear velocity at the time of injection corrects a peak area based on the linear velocity at the time of the sample injection for every sample component.

When the peak area correction unit 40 according to the linear velocity at the time of injection is provided, the control unit 20 is preferably further provided with a linear velocity conversion table holding section 38 for holding a linear velocity conversion table. In that case, the peak area correction unit 40 according to the linear velocity at the time of injection corrects a peak area using the linear velocity conversion table currently held by the linear velocity conversion table holding section 42.

As is also applicable to the case when the electric current value at the time of sample injection changes, the control units 20 and 20a are preferably provided with a current integral value calculation unit 42, and the correction unit 32 is preferably provided with a peak area correction unit 44 according to a current integral value. The current integral value calculation unit 42 incorporates an electric current value at the time of sample injection from the high voltage power supply 8 and calculates that current integral value. The peak area correction unit 44 according to the current integral value corrects a peak area based on the current integral value calculated by the current integral value calculation unit 42.

The correction unit 32 is provided with the peak area correction unit 36 according to the relative mobility as an indispensable element. Either one or both of the peak area correction unit 40 according to the linear velocity at the time of injection and the peak area correction unit 44 according to the current integral value are provided. As a result, it is possible to obtain a peak area output value in which either one or both of the following corrections are made in addition to the correction by the peak area correction unit 36 according to the relative mobility: the correction by the peak area correction unit 40 according to the linear velocity at the time of injection and the correction by the peak area correction unit 44 according to the current integral value. These are shown in the outputs in FIG. 3 by the solid line, dashed line, and dash-dotted line. The path shown by the two-dot chain line is a comparative example, showing the case where the peak area correction unit 40 according to the linear velocity at the time of injection and the peak area correction unit 44 according to the current integral value are not provided, in which the peak area output value corrected only by the peak area correction unit 36 according to the relative mobility is obtained as the corrected peak area output value.

Figure 4:
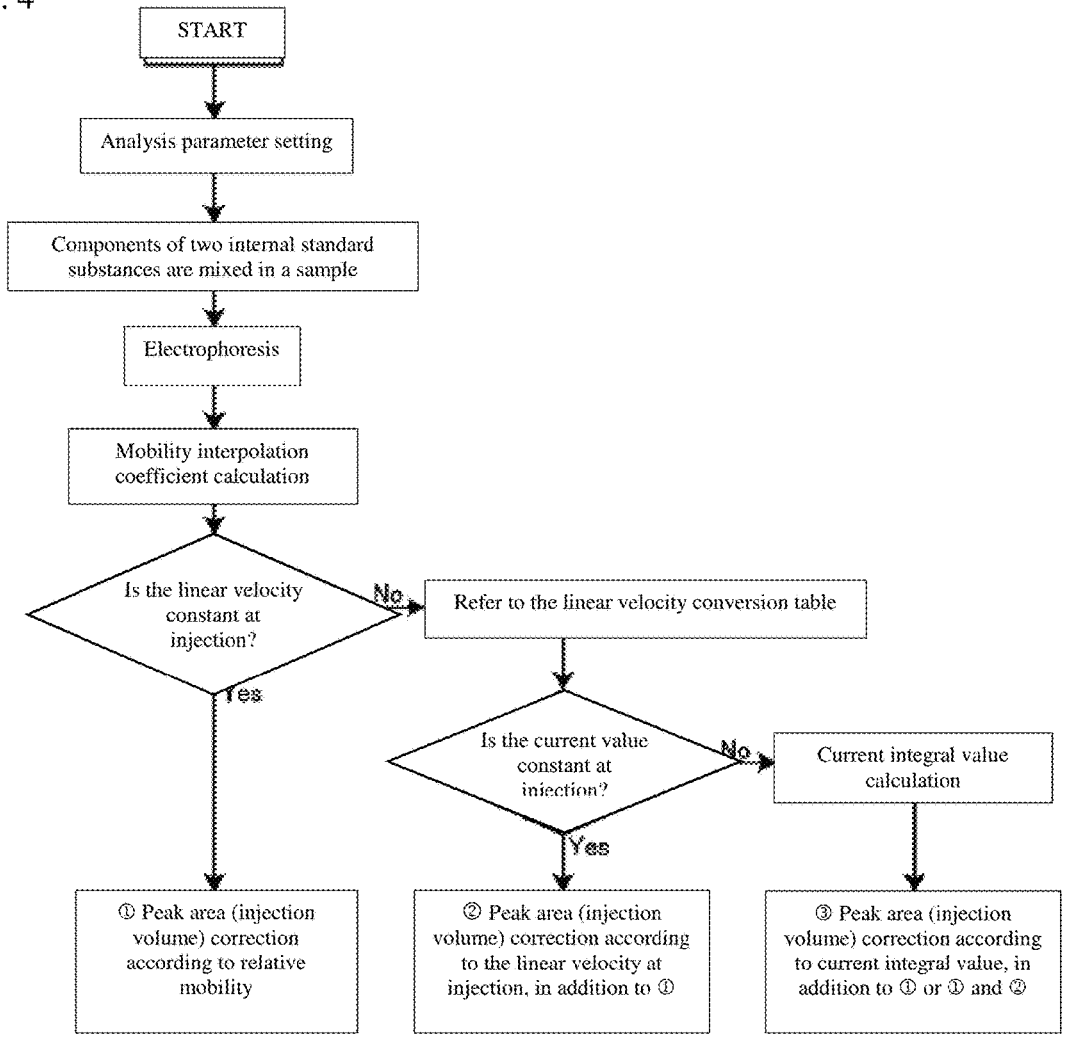
FIG. 4 is a flow chart illustrating a capillary electrophoresis method of one example of embodiment.

FIG. 4 is a flow chart illustrating the electrophoresis method of one example of embodiment. The case where an electrophoresis flow path is the capillary 2 will be explained here; however, the correction operation is also the same even when the electrophoresis flow path is the electrophoresis flow path 24 of a plate. Although there are differences in the electrophoresis operation for carrying out a sample injecting operation to the capillary 2 or the electrophoresis flow path 24, and carrying out separation, the differences were already described above.

First, analytical parameters (a sample injection voltage, an injection time, and an electrophoresis voltage) are established. Two kinds of internal standard substances A and B are mixed in a sample. The internal standard substance A is an internal standard substance with smaller mobility than that of any sample component, and the internal standard substance B is an internal standard substance with larger mobility than that of any sample component.

The injection end of the capillary 2 is immersed in the sample of the specimen container 12, the other end of the capillary 2 is immersed in the buffer solution 6, a voltage is applied to between both ends of the capillary 2, and the sample is electrically injected into the capillary 2. The quantity of the sample stored in the specimen container 12 is set so as to increase more than the quantity injected into the capillary 2 at the injection time.

The injection end of the capillary 2 is taken out from the sample after the sample injection and immersed in the buffer solution 4, a voltage is applied to between both ends of the capillary 2, and the electrophoresis and separation of the sample is carried out at the capillary 2.

The separated sample component is detected by the detector 14, and the peak area for every sample component is determined.

The mobility interpolation coefficient Fi of each sample component is calculated from the peak detection time of the internal standard substances A and B and the peak detection time of each sample component. The mobility interpolation coefficient Fi will be described later with reference to FIG. 5.

When the linear velocity of the sample component injection to the time of injection is constant, i.e., when an intercalator pigment is not mixed in a separation medium, the peak area of each sample component, i.e., an injection volume, is corrected using the mobility interpolation coefficient Fi as the relative mobility. The method of correction will also be mentioned below.

When the linear velocity of the sample component injection at the time of injection is not constant, i.e., when an intercalator pigment is mixed in a separation medium, the linear velocity at the time of the sample injection for every sample component is obtained with reference to the linear velocity conversion table prepared in advance.

Next, when the electric current value at the time of injection is constant, for example, when the electric current value at the sample injection time is 5% or less, in addition to the correction of the peak area according to the relative mobility, a correction of the peak area according to the linear velocity at the time of injection, i.e., the correction of the injection volume, is further performed.

When the electric current value at the time of injection is not constant, the electric current value is integrated by an ammeter of the high voltage power supply 8 over the injection time. In this case, in addition to the correction of the peak area according to the relative mobility and in addition to the correction of the peak area according to the relative mobility and the correction of the peak area according to the linear velocity at the time of injection, the peak area according to the current integral value is also corrected.

Next, the methods of correction will be described in details.

(1) Correction Using Two Kinds of Internal Standard Substances

In general, in the method of electrically injecting a sample into a capillary, the effective injection volume (Vi) of each ion component in a sample can be expressed by $$V_i = t_{inj} v_i (\pi r^2)$$

Where
tinj: an injection time,
vi: a linear velocity in case each ion is injected from a capillary end, and
r: a capillary radius.

The following equation represents those without a hydrodynamic movement speed component generated according to a head difference (pressure differential) between both ends of the capillary and without a velocity component generated by electroosmotic flow with an ignorable small zeta potential between the capillary wall and the solution:

$$v_i = \mu_i E_{inj}$$

(Einj is an electric field strength at the time of injection, and μi is the mobility of each ion component); therefore, injection volume Vi becomes $$V_i = t_{inj} E_{inj} (\pi r^2) \cdot \mu_i$$

and is proportional to μi. This is illustrated by FIG. 5, and the inclination (proportionality constant) thereof is $$\pi r^2 t_{inj} E_{inj}$$

Figure 5:
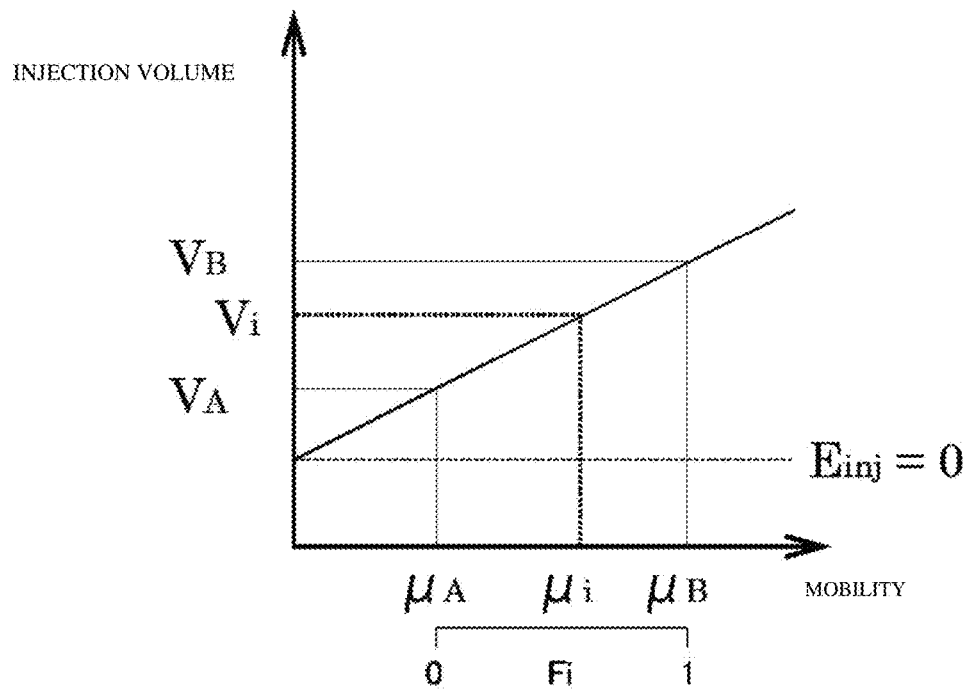
FIG. 5 is a graph showing the relation between the injection volume and the mobility of a sample component.
Figure 6A:
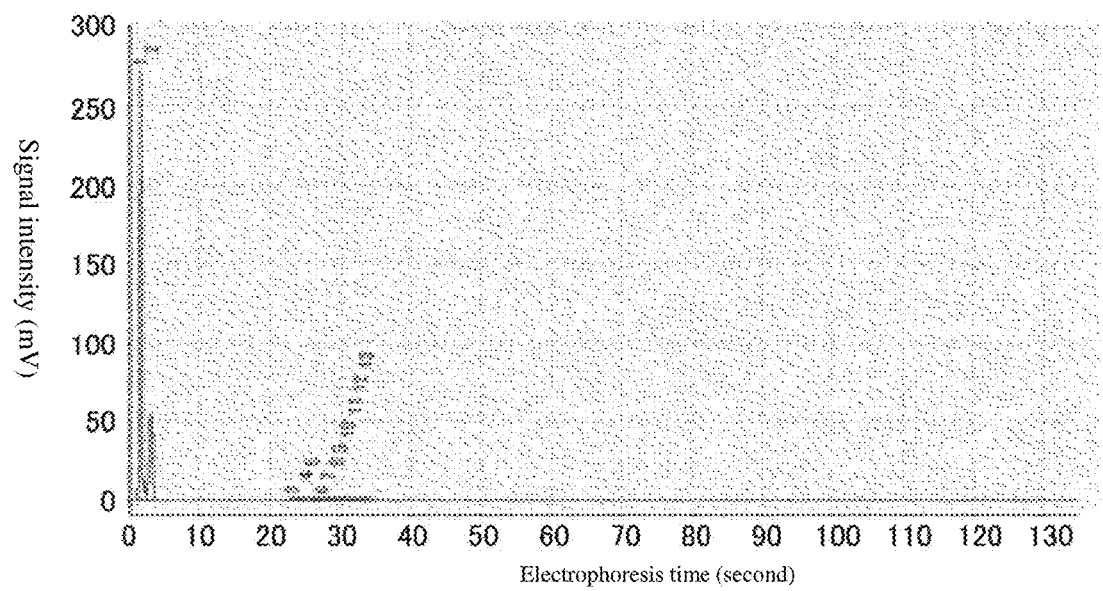
FIG. 6A-FIG. 6E is a drawing of an electrophoresis waveform showing the relation between the distance from a capillary injection end and a separation peak waveform.
Figure 6B:
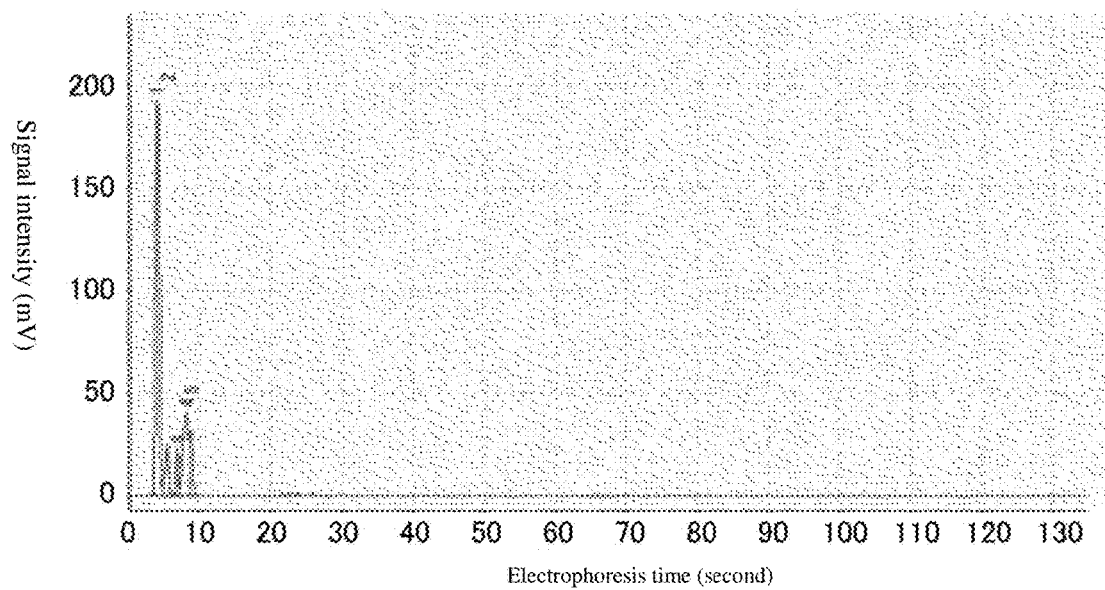
Figure 6C:
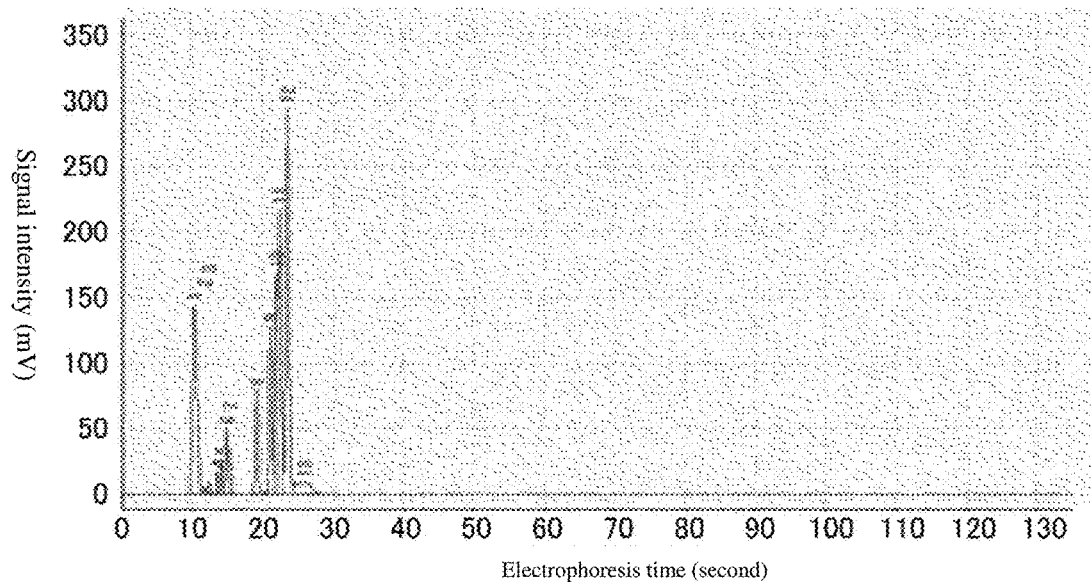
Figure 6D:
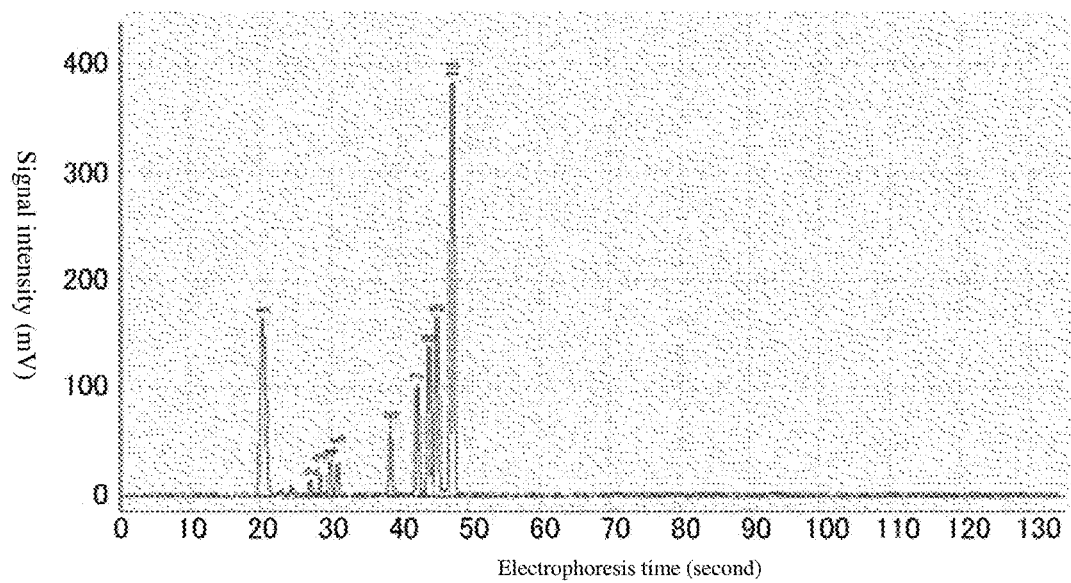
Figure 6E:
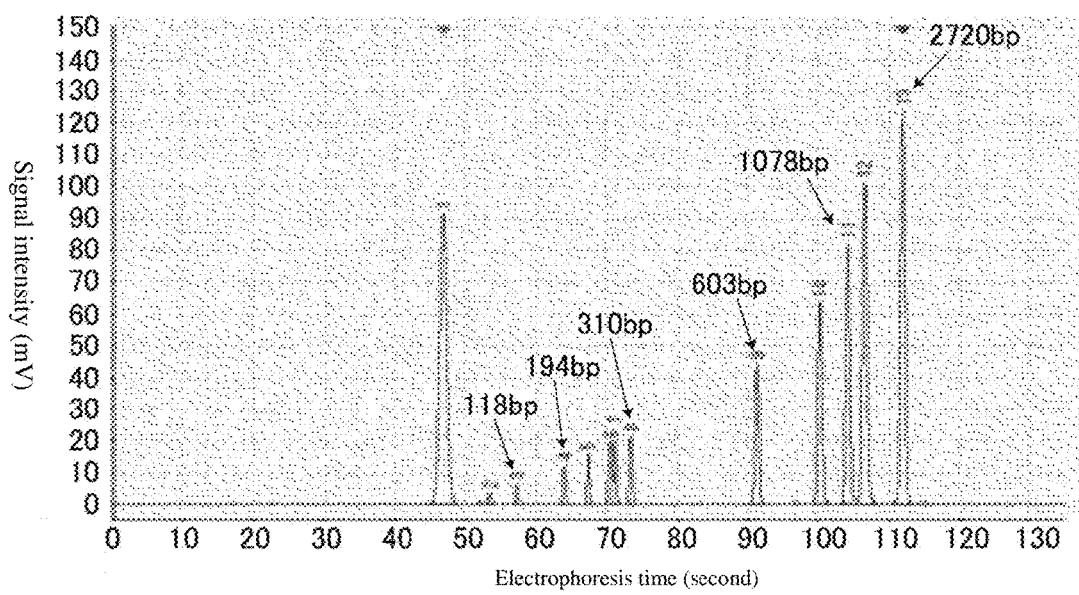

When two types of internal standard substances, the internal standard substance A with smaller mobility than that of any sample component (injection volume $V_A$) and the internal standard substances B with larger mobility than that of any sample component (injection volume $V_B$), are added in a sample, as shown in FIG. 5, the relative mobility with respect to any component i can be obtained as an interpolation coefficient F. The interpolation coefficient F is standardized so that mobility μA of the internal standard substance A is 0 and mobility μB of the internal standard substance B is 1. Interpolation coefficient Fi with respect to any component i is obtained by the following mathematical equations (1) and (2).

$$V_i = F_i V_B + (1 - F_i) V_A \quad (1)$$

$$F_i = (V_i - V_A)/(V_B - V_A) \quad (2)$$
$$= (v_i - v_A)/(v_B - v_A)$$
$$= (\mu_i - \mu_A)/(\mu_B - \mu_A)$$

Approximation is made with those that move to a detection unit using the linear velocity v as is when ions are injected from the sample injection end of a capillary. When L is a separation length from the sample injection end of a capillary to a detection unit, and t is a peak detection time in a detection unit, the linear velocity v becomes v=L/t. Mobility μ can be obtained by the following equation:

$$\mu = v/E_{inj} = L/E_{inj} t$$

In the example of embodiment described below, the electric field strength Einj at the time of injection is 200 V/cm, the separation length from a sample injection end to a detection unit is 8.5 cm, and the mobility μ (μi, μA, μB) is obtained at a unit of (cm²/V seconds) from the peak detection time t obtained experimentally. Thus, the obtained mobility μ (μi, μA, μB) applies to equation (2) and the interpolation coefficient Fi for any component i can be calculated.

The correction of the peak area of any component i is preferably performed by the following steps.

1) A peak area is obtained on the electrophoresis pattern of the time axis indicated by a horizontal axis.

2) A peak area is obtained after converting the horizontal axis of the electrophoresis pattern from the time axis to a mobility axis.

$$\text{(Peak area)} = \sum_n h_n \times \Delta \mu_n$$

-continued $$= \sum_n h_n \times (\mu_{n+1} - \mu_n)$$

Here, hn represents a peak height and μn represents mobility.

3) The obtained peak area of any component with regard to the mobility axis is corrected using an interpolation coefficient Fi. If the peak area and the concentration of the internal standard substance B are $A_B$ and $C_B$, respectively, concentration Ci before correction of any component is Ci=(Ai/$A_B$)×$C_B$, and the concentration Cic after the correction is Cic=Fi×Ci.

(2) Correction in a System Containing an Intercalator Pigment

In a DNA fragment analysis, there is a capillary electrophoresis analysis method in which, after a capillary is filled up in advance using a separation buffer solution containing an intercalator pigment as a separation medium, a sample is injected from a capillary injection end by means of an electric injection method. With this method, it is not necessary to label the sample with a fluorescent dye in advance; a fluorescence detection becomes possible by a detection unit by allowing the sample DNA injected from the capillary injection end and an intercalator pigment to form a complex.

In this electrophoresis analysis method using an intercalator pigment, since an electric charge changes in the process in which the sample DNA and an intercalator pigment form a complex, the injection rate of a sample component is not constant.

Figure 7:
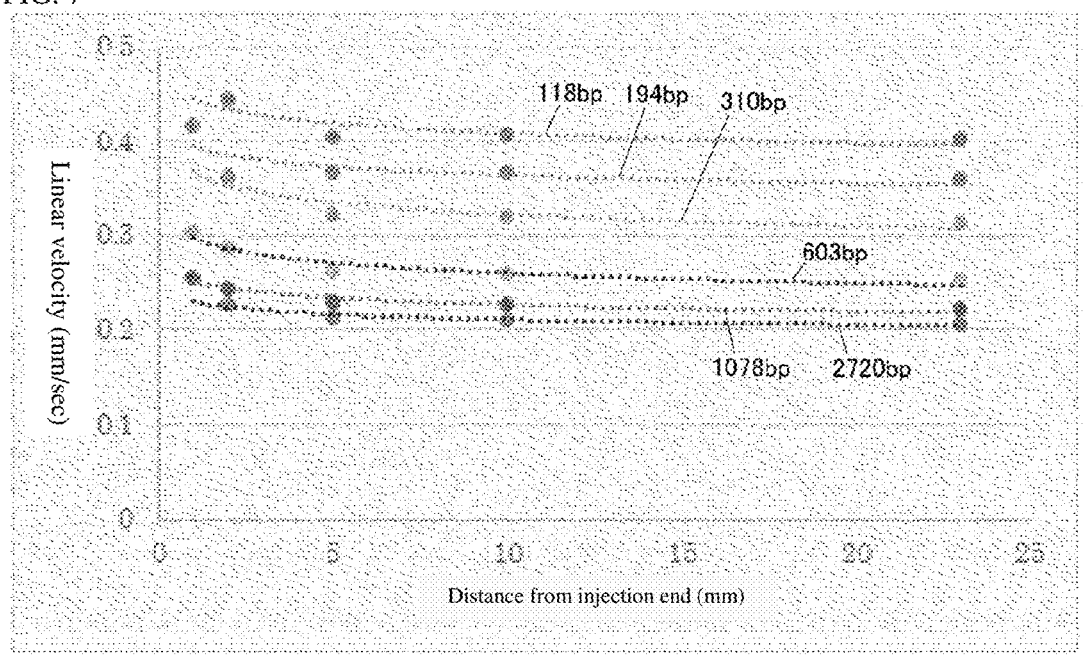
FIG. 7 is a graph illustrating the relation between the linear velocity and the distance from the injection end for every DNA sample component that differs in size based on the data of FIG. 6.

For example, the distance from an injection end and an electrophoresis waveform are measured at any position in a capillary using a device that can detect the fluorescence of a complex. FIGS. 6A-6E show the electrophoresis waveforms in the position whose distances from an injection end is 1 mm, 2 mm, 5 mm, 10 mm, and 23 mm, respectively. FIG. 7 shows the relation between the distance from an injection end and the movement speed based on those measurement results.

However, in the measurement in which the measurement results of FIG. 6 and FIG. 7 were obtained, in order to eliminate the influence of the mobility change by the EKI itself, unlike the example of embodiment, a full volume injection system using a crossing flow path was adopted. The sample was a HaeIII digest (product of Promega Corp.) of φX174 DNA. A separation medium contained Gelstar (registered trademark) by 20,000-time dilution as an intercalator pigment in a separation buffer solution (DNA-1000: product of Shimadzu Corp.).

As can be seen from FIG. 7, the speed at which the inside of a capillary is subjected to electrophoresis according to the distance from an injection end is gradually decreasing. This is due to the change in the net charge by performing electrophoresis while forming a complex with the DNA that has a negative charge and an intercalator pigment that has a positive charge. Although it seems that there is a minor difference in the injection volume according to the sample component near the injection end, the mobility changes with the injection time according to the electric charge of DNA-pigment complex, and the introduction amount changes along with it.

Then, as one embodiment, the linear velocity conversion table for every DNA size is prepared according to the injection time under predetermined conditions, and the injection volume with respect to the component with a known size is corrected.

Figure 8:
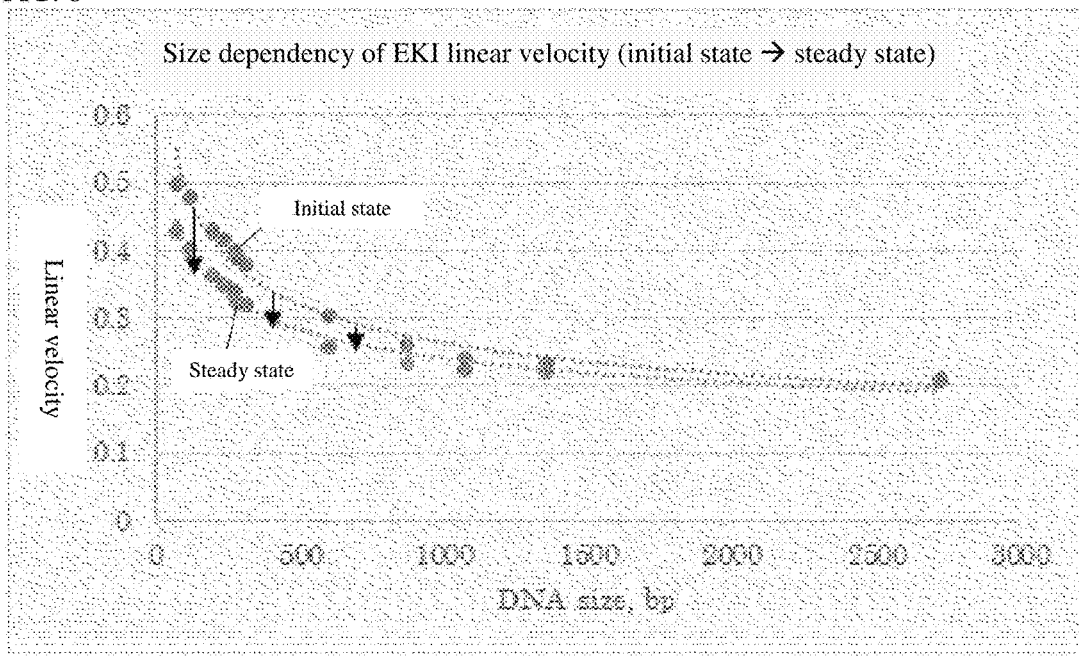
FIG. 8 is a graph illustrating the relation of the DNA sample component size and the linear velocity based on the same data according to the initial state (the upper side of the graph) and the steady state (the lower side of the graph) of an injection.

The composition of a separation medium, the type and the concentration of an intercalator pigment, injection parameters, and other parameters are the conditions that should be specified when creating a linear velocity conversion table. FIG. 8 shows the relation of the linear velocity to a DNA fragment size from the same experiment data shown in FIG. 7. It was found that the "breaking effect" at the time of the sample injection by an intercalator is significant, the shorter the DNA strand length is.

The ratio of the (initial state)/(steady state) in FIG. 8 is a "linear velocity conversion factor." The example of the linear velocity conversion table obtained here is shown in Table 1.

TABLE 1

| DNA size | Linear velocity conversion coefficient |
|---|---|
| 118 bp | 1.236 |
| 194 bp | 1.181 |
| 310 bp | 1.061 |
| 603 bp | 1.127 |
| 1078 bp | 1.067 |
| 2720 bp | 1.050 |

The injection volume for every sample component is multiplied by a linear velocity conversion coefficient to become an injection volume correction value. The injection volume is preferably the injection volume after a correction is carried out according to the mobility.

(3) Correction in Case the Monitor Current at the Time of Injection Changes

When a separation buffer solution is used as a separation medium, the salt concentration of a sample is the same as the salt concentration of the separation buffer solution; when there is no temperature change according to the application of voltage, an electric current value is proportional to the voltage. Since the movement speed of a sample component is proportional to the electric current value, it is also properly proportional to the applied voltage. In that case, under the electrophoresis voltage fixed with time, the electric current value at the time of injection is also constant with time, and the electrophoresis waveform of a sample component turns into a rectangle.

It is possible to determine whether the electric current value at the time of injection is constant or not when the range of fluctuation from the instruction of an ammeter is within 5% (the portion equivalent to the change in temperature), for example.

However, when the salt concentration of a sample is not in agreement with that of the separation buffer solution, or when there is a change in temperature, an electric current value generally does not become constant over time even if the applied voltage is constant over time.

Movement speed vinj at the time of sample injection is expressed by the following equation.

$$v_{inj} = K_a / \pi r^2$$

Here, Ka is a constant determined by the pH of the separation buffer solution, dielectric constant, ionic strength, viscosity, DNA strand length, potential difference (zeta potential) between the capillary wall and the electrophoresis solution, and other factors.

The following formula can define the injection volume $n_a$, current I (t), and concentration $c_a$ (x, t) at a distance x from an injection end for an injection time t.

$$dn_a(x,t) = K_a c_a(x,t) \times I(t) dt$$

The injection time tinj is short and $c_a(x, t)$ can be regarded as constant $c_a$, so the injection volume when the injection time tinj has passed becomes:

$$n_a = K_a * c_a \int_0^{t_{inj}} I(t) dt$$

Figure 9:
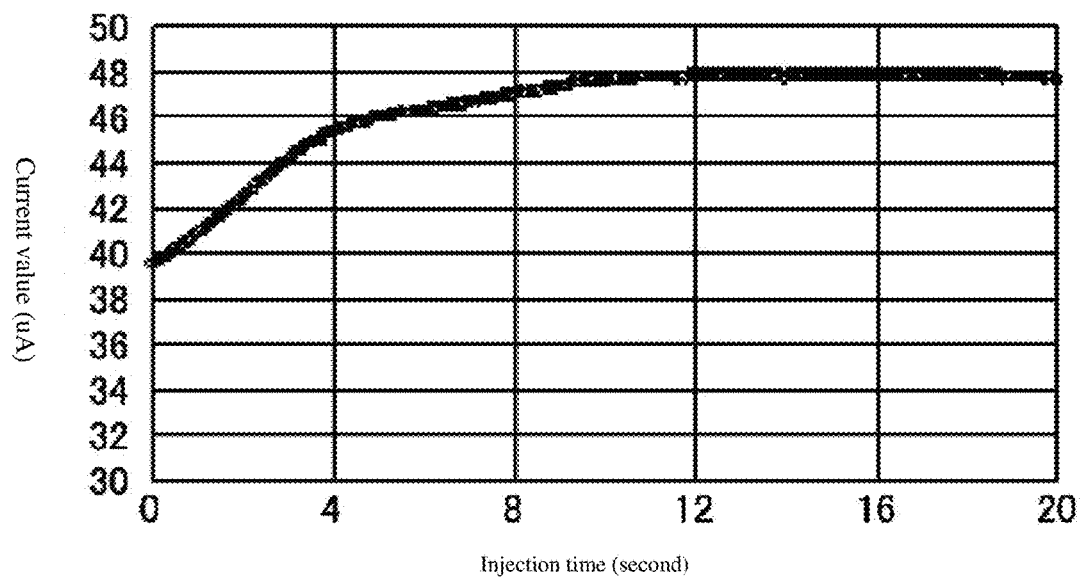
FIG. 9 is a graph illustrating a temporal change of the electric current value at the time of sample injection.

An example of the current waveform at the time of sample introduction is shown in FIG. 9. This shows the electric current value at the time of launching from the start of sample injection until 20 seconds. The electric current value rises from immediately after the start of sample injection, indicating that it becomes steady from around 10 seconds, and the sample injection volume is changing over time for 10 seconds from the start of sample injection.

Since the movement speed of a sample component is proportional to the electric current value, the sample injection volume is proportional to the current integral value at the time of sample injection. Therefore, the current integral value at the time of sample injection is detected, and a correction is carried out where the sample injection volume is proportional to the current integral value.

Since the current at the time of sample injection expresses the motion of all components in a capillary, it is also useful for monitoring the repeat accuracy during analysis.

Examples of Embodiment

The results of carrying out the quantitative analysis of the sample component subjected to capillary electrophoresis separation carried out by the method of one embodiment are shown below.

The analysis conditions are as follows.

Capillary: 50 µm in inner diameter×85 mm in effective length, LPA (linear polyacrylamide) coated capillary Separation buffer solution: DNA-1000 (product of Shimadzu Corp.)

Intercalator: GelStar (registered trademark) diluted 20,000 times

Sample: φX174-HaeIII digest (1 ng/µL) (product of Promega Corp.)

Injection conditions: 200 V/cm×3 seconds

Separating condition: 200 V/cm

Figure 10:
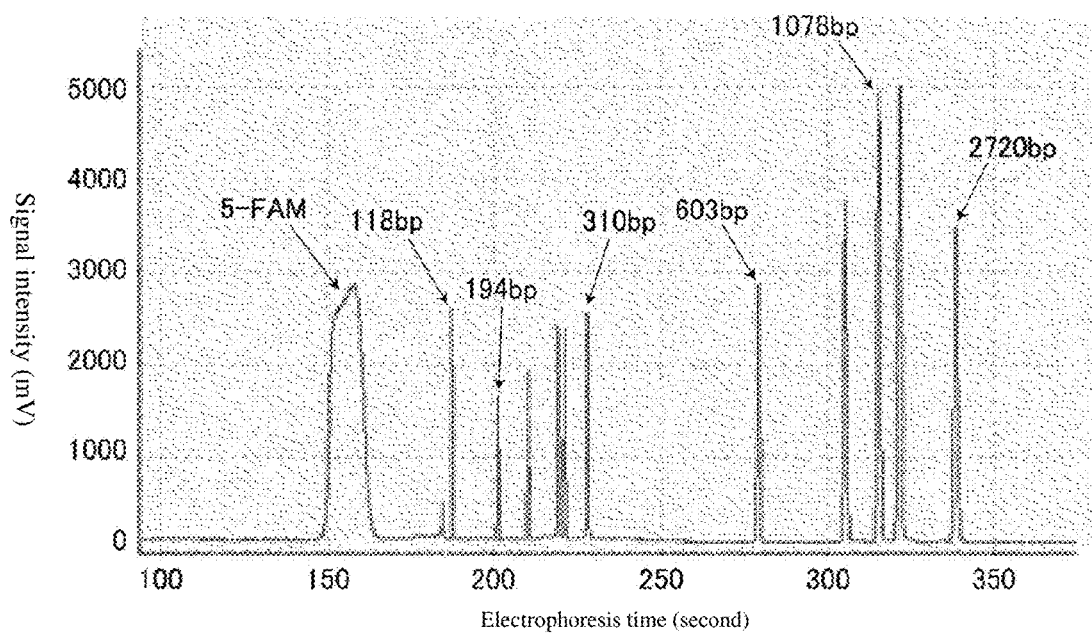
FIG. 10 is a drawing illustrating the electrophoresis waveform in one example of embodiment.

The obtained electrophoretic pattern is shown in FIG. 10. A sample is mixed with a fluorescent dye (5-FAM) unrelated to DNA, subjected to electrophoresis, and used as a marker with larger mobility than any sample. The DNA fragment sample of 2720 bp is used as an internal standard substance with the smallest mobility.

Figure 11:
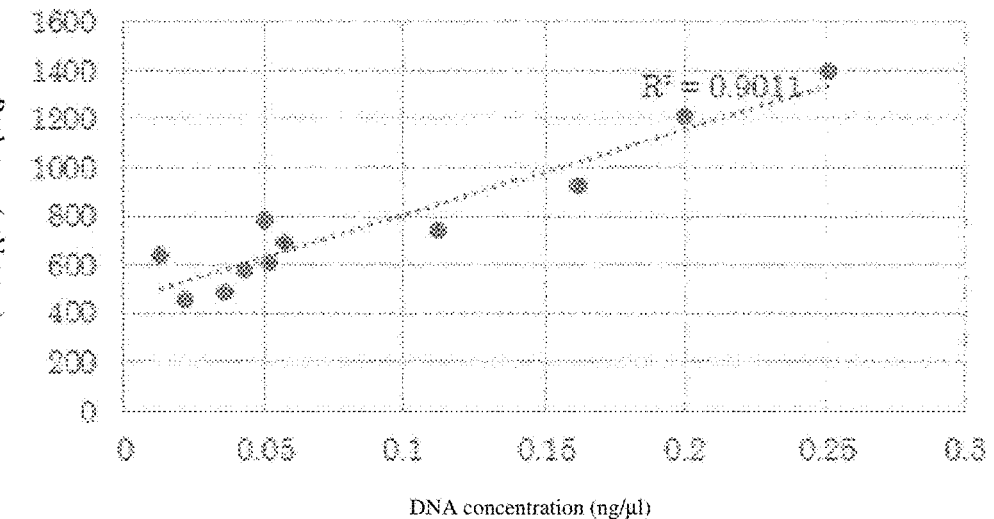
FIG. 11 is a graph shown by the time axis standard when each sample component concentration and the peak area of the same example of embodiment were measured as-is.

Based on the data of an electrophoresis waveform of FIG. 10, the result of plotting each theoretical concentration (ng/µL) and peak area value is shown in FIG. 11 on 11 peaks of the DNA fragment sample except 2720 bp. Coefficient of determination $R^2$ was 0.9011. The theoretical concentrations are the known concentration before enzyme digestion and the concentration of each DNA fragment sample obtained from the DNA strand length in total.

Figure 12:
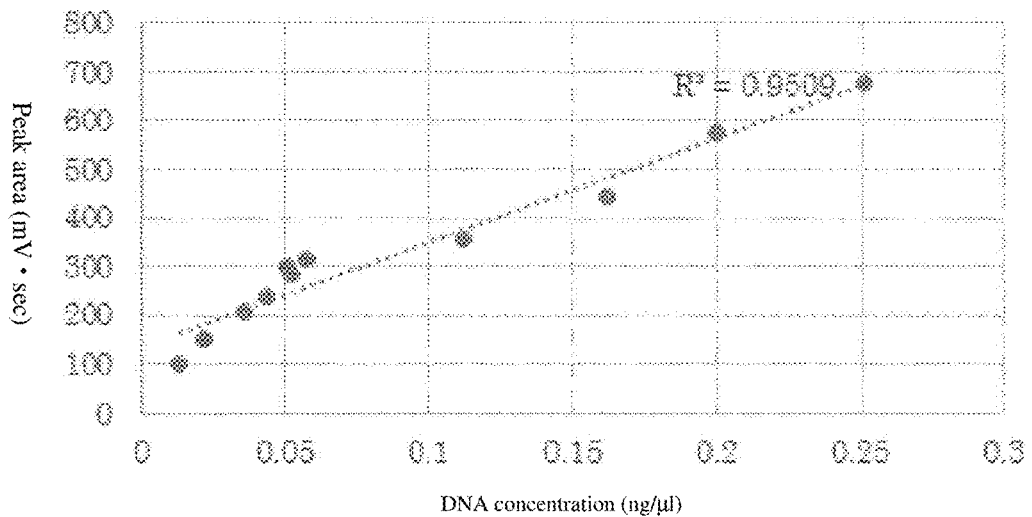
FIG. 12 is a graph in which the time axis of the data of the graph in FIG. 11 is converted to a mobility axis and shown by a mobility axis reference.

Next, when the time axis of the electrophoretic pattern was converted to the mobility axis, and the peak area of the mobility axis reference was determined, as shown in FIG. 12, the coefficient of determination $R^2$ was improved to 0.9509.

Figure 13:
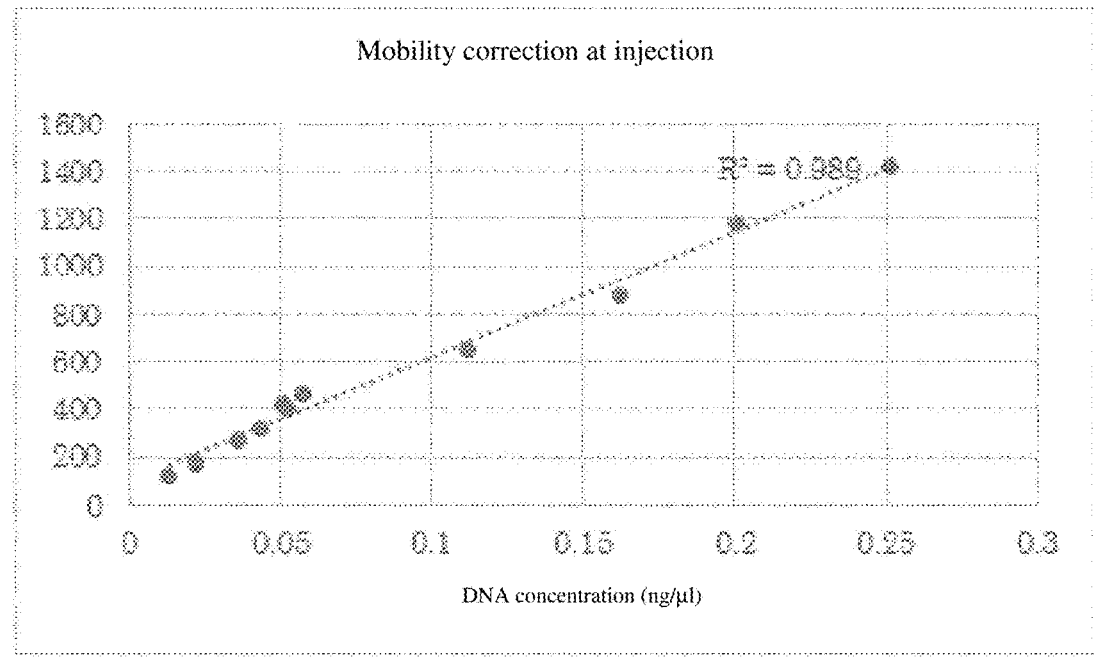
FIG. 13 is a graph illustrating the relation of each sample component concentration and a peak area after performing a correction according to the mobility to the data of the graph in FIG. 12.

As a result of correcting the peak area of each component obtained on a mobility axis using interpolation coefficient Fi, as shown in FIG. 13, the coefficient of determination $R^2$ was improved to 0.989. Thus, it was found that the quantification accuracy of the quantity corresponding to the peak area detected improves, i.e., the peak area detected by correcting the injection volume for every sample component based on the relative mobility of a sample component.

Figure 14:
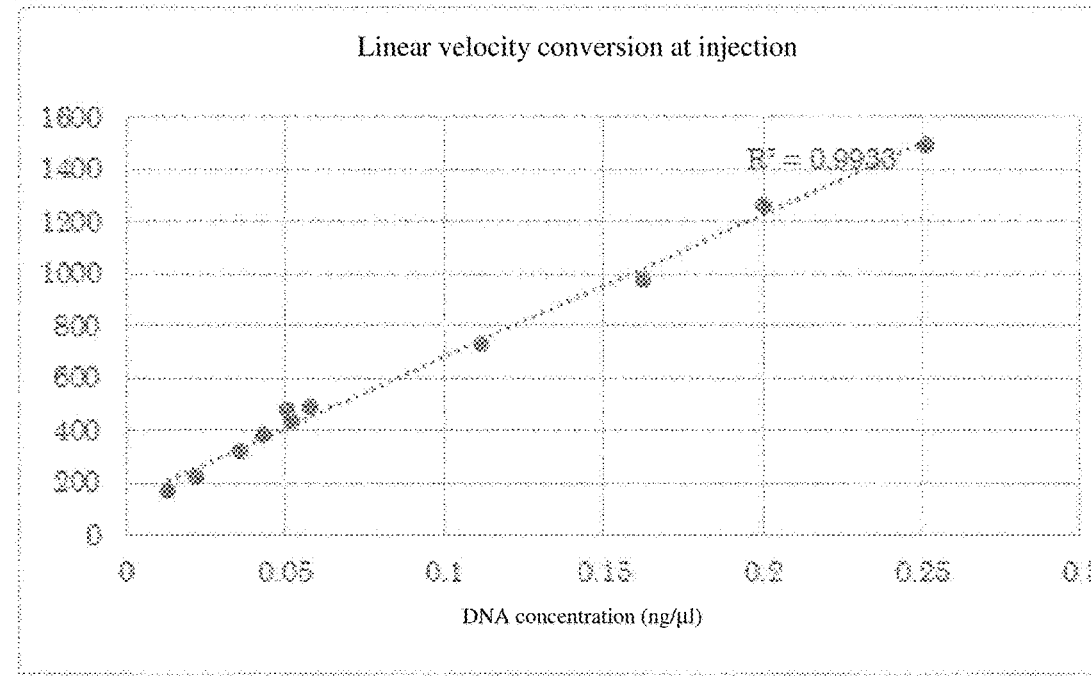
FIG. 14 is a graph illustrating the relation of each sample component concentration and a peak area after further performing a correction according to the linear velocity by an intercalator to the data of the graph in FIG. 13.

Next, FIG. 14 shows the result of performing a correction according to the linear velocity at the time of injection by an intercalator pigment using the linear velocity conversion coefficient shown in Table 1 with respect to the data shown in FIG. 13. The linear velocity conversion coefficient of the DNA size, not shown in Table 1, was calculated by linear interpolation based on the linear velocity conversion coefficient of the DNA size shown in Table 1. Coefficient of determination $R^2$ was improved to 0.9933 in the data shown in FIG. 14. Thus, it was found that, by correcting the injection volume for every sample component based on the linear velocity at the time of the sample injection for every sample component, the quantification accuracy of the quantity corresponding to the peak area detected further improves.

EXPLANATIONS OF REFERENCES

2 Capillary
4 and 6 Buffer solution
8 High voltage power supply
10 Syringe pump
12 Specimen container
14 and 14a Detection unit
20 and 20a Control unit
24 Electrophoresis flow path
30 Peak area calculation unit
32 Correction unit
36 Peak area correction unit according to relative mobility
38 Linear velocity conversion table holding section
40 Peak area correction unit according to the linear velocity at the time of injection
42 Area integral value calculation unit
44 Peak area correction unit according to the area integral value

What is claimed:

1. An electrophoresis method for carrying out a quantitative analysis of sample components in which electrophoretic separation is carried out, the method comprising:
   (A) electrically injecting a sample containing a plurality of sample components different in size from each other into a gel-filled electrophoresis flow path through one end thereof;
   (B) subjecting the injected sample to electrophoresis to separate the sample components according to their size by applying a voltage to both ends of the electrophoresis flow path;
   (C) detecting the separated sample components at a detection position of the electrophoresis flow path;
   (D) obtaining a peak area of each of the detected sample components; and
   (E) correcting the obtained peak area for each of the sample components based on an injection rate of each sample component, wherein
   the correction based on the injection rate in step (E) includes (E1) a correction based on a relative mobility according to the size of each sample component, and:
   (E2) a correction based on a change in linear velocity at a time of sample injection for each sample component resulting from an intercalator disposed in the electrophoresis flow path.

2. The electrophoresis method according to claim 1, wherein in the step (A), two kinds of internal standard substances, internal standard substance A with smaller mobility than that of any sample component and internal standard substance B with larger mobility than that of any sample component, are injected into the electrophoresis flow path along with a sample, and in the correction (EI), an interpolation coefficient Fi for every sample component is used as the relative mobility; where the interpolation coefficient Fi is a standardized coefficient so that a mobility μA of the internal standard substance A is 0 and a mobility μB of the internal standard substance B is 1.

3. The electrophoresis method according to claim 1, wherein a linear velocity conversion table for every sample component obtained in advance under specific conditions is used as the correction (E2).

4. The electrophoresis method according to claim 2, wherein a linear velocity conversion table for every sample component obtained in advance under specific conditions is used as the correction (E2).

5. An electrophoresis device, comprising:
an electrophoretic section including:
an electrophoresis flow path filled with gel,
an electric power supply configured to apply a voltage for electrophoresis in the electrophoresis flow path and to both ends of the electrophoresis flow path and separate a plurality of sample components according to their size, and
a detector for detecting the sample components separated in the electrophoresis flow path, and
a controller that obtains an electrophoretic signal from the detector and carries out a quantitative analysis for every sample component; the controller including:
a peak area calculation unit configured to determine a peak area of the sample components from the electrophoretic signal, and
a correction unit configured to correct the determined peak area for each of the sample components based on an injection rate for every sample component; the correction unit including;
a first peak area correction unit configured to correct the determined peak area based on a relative mobility of the sample component, according to a size of each sample component; and
a controller that obtains an electrophoretic signal from the detector and carries out a quantitative analysis for every sample component; the controller including:
a peak area calculation unit configured to determine a peak area of the sample components from the electrophoretic signal, and
a correction unit configured to correct the determined peak area for each of the sample components based on an injection rate for every sample component; the correction unit including;
a first peak area correction unit configured to correct the determined peak area based on a relative mobility of the sample component, according to a size of each sample component; and
a second peak area correction unit configured to correct the determined peak area based on a change in linear velocity at a time of sample injection for every sample component resulting from an intercalator disposed in the electrophoresis flow path.

6. The electrophoresis device according to claim 5, wherein the electrophoresis device further comprises a linear velocity conversion table storing section for storing a linear velocity conversion table for every sample component; and
wherein the second peak area correction unit is conjured to correct the determined peak area according to the linear velocity at the time of injection is configured to use the linear velocity conversion table stored in the linear velocity conversion table storing section.

7. The electrophoresis device according to claim 5, wherein the controller further comprises a current integral value calculation unit that incorporates an electric current value at the time of sample injection from the electric power supply and calculates the current integral value; and
a third peak area correction unit that is configured to perform an injection rate-based correction based on the current integral value obtained by the current integral value calculation unit.

8. The electrophoresis device according to claim 6, wherein the controller further comprises a current integral value calculation unit that incorporates an electric current value at the time of sample injection from the electric power supply and calculates the current integral value; and
a third peak area correction unit that is configured to perform an injection rate-based correction based on the current integral value obtained by the current integral value calculation unit.

* * * * *